(12) United States Patent
Kjellmann Bruun et al.

(10) Patent No.: US 7,571,804 B2
(45) Date of Patent: Aug. 11, 2009

(54) PACKAGE FOR A MEDICAL DEVICE

(75) Inventors: Bo Kjellmann Bruun, Copenhagen O (DK); Lotte M. Klixbull, Copenhagen V (DK); Jan Torstensen, Virum (DK)

(73) Assignee: Coloplast A/S, Humlebaek (DK)

( * ) Notice: Subject to any disclaimer, the term of this patent is extended or adjusted under 35 U.S.C. 154(b) by 864 days.

(21) Appl. No.: 11/070,283

(22) Filed: Mar. 3, 2005

(65) Prior Publication Data

US 2006/0196783 A1 Sep. 7, 2006

(51) Int. Cl.
*B65D 83/10* (2006.01)
(52) U.S. Cl. .................. 206/210; 206/222; 206/364
(58) Field of Classification Search ............ 206/205, 206/210, 219, 222, 363, 364, 365
See application file for complete search history.

(56) References Cited

U.S. PATENT DOCUMENTS

| | | | |
|---|---|---|---|
| 3,648,704 A | 3/1972 | Jackson | |
| 3,898,993 A | 8/1975 | Taniguchi et al. | |
| 3,967,728 A | 7/1976 | Gordon et al. | |
| 4,206,843 A * | 6/1980 | Rainey | 206/216 |
| 4,362,241 A * | 12/1982 | Williams | 206/210 |
| 4,754,877 A * | 7/1988 | Johansson et al. | 206/364 |
| 6,634,498 B2 | 10/2003 | Kayerød et al. | |
| 2005/0015076 A1 | 1/2005 | Giebmeyer et al. | |

FOREIGN PATENT DOCUMENTS

| | | |
|---|---|---|
| DE | 10213411 | 10/2003 |
| WO | WO 97/26937 | 7/1997 |
| WO | WO 98/11932 | 3/1998 |
| WO | WO 99/30761 | 6/1999 |
| WO | WO 01/43807 | 6/2001 |
| WO | WO 2004/075944 | 9/2004 |

* cited by examiner

*Primary Examiner*—Jacob K Ackun, Jr.
(74) *Attorney, Agent, or Firm*—Jacobson Holman PLLC

(57) ABSTRACT

An assembly for wetting a medical device, in particular a urinary catheter, with a fluid medium is provided. The device is packed in a package which contains the fluid medium confined in a compartment. To ensure wetting of the device, the package is adapted to open the compartment and the package in one and the same opening action, preferably so that the compartment opens at the latest when the package opens. In that way, removal of the device from the package requires opening of the compartment and the device is therefore wetted automatically as part of the opening procedure.

17 Claims, 7 Drawing Sheets

PACKAGE FOR A MEDICAL DEVICE

The invention relates to an assembly for wetting a medical device with a fluid medium, e.g. for wetting a catheter, such as a urinary catheter, e.g. with an antimicrobial agent, or a lubricant, or a saline solution for activating a hydrophilic low-friction surface. The assembly comprises a package accommodating the medical device and a compartment accommodating the fluid medium so that the fluid medium is not in contact with the medical device.

BACKGROUND OF THE INVENTION

Often, medical devices such as catheters must be wetted by a liquid medium prior to use. As an example, it is typically desired to wet a medical device with an antimicrobial agent or with a substance for controlling the surface friction of the device. In one example, a medical catheter, e.g. a urinary catheter for draining the bladder, must be inserted into the body through a natural or artificial body passage, e.g. the urethra. To facilitate the insertion, a friction reducing substance is normally applied to the catheter. In the remaining part of this text, the invention is referred to in relation to a urinary catheter but the skilled person would readily derive other applications of the invention, e.g. catheters for blood vessels, respiratory system ventilation, etc.

Catheters for draining the bladder are used for intermittent as well as indwelling or permanent catheterisation. Typically, catheters are used by patients suffering from urinary retention, e.g. para- or tetraplegics who may have no control permitting voluntary urination. Catheters with low friction surface characteristics towards body tissue, e.g. a lubricated surface or a surface with a hydrophilic surface coating have been developed to facilitate insertion of the catheter into the body.

Typically, catheters are delivered in a completely sealed and sterilised package which, in addition to the catheter, may accommodate a substance which activates the low-friction characteristics of the catheter surface. Some of the existing packages provide the substance in a compartment which separates the substance from the catheter, e.g. in a pouch or in a small plastic bottle. Prior to the insertion of the catheter, the user must manipulate and empty the compartment for the content to be brought into contact with the catheter. Since the user's dexterity is sometimes reduced, the manipulation of the compartment inside the package can be difficult.

DESCRIPTION OF THE INVENTION

It is an object of the invention to facilitate wetting of a medical device, e.g. with respect to preparation of a urinary catheter before insertion into the body. Accordingly, the invention provides an assembly of the kind mentioned in the introduction and characterised in that the assembly comprises opening means adapted for a combined opening action whereby the package as well as the compartment are opened. Due to the combined opening action, the compartment can be emptied as an integrated part of the opening procedure, and the risk of misuse, e.g. by forgetting to apply the fluid medium to the medical device prior to use, is reduced.

The combined opening action could be an opening action where the user opens the package and the compartment with one single grip in the assembly, or the combined opening action could be where the user moves one single component relative to another component of the assembly, which movement thereby opens both the package and the compartment. The component could preferably be moved back and/or forth in one single direction, e.g. back and forth along an axis or clockwise and anticlockwise around an axis whereby the compartment and the package opens. The combined opening action could be provided by any means which prevent opening of the package and/or exposure of the medical device for the use thereof without opening of the compartment.

The medical device could be of any kind, and as aforementioned, the device could be a catheter of the kind known in the art, i.e. comprising an elongate body extending between a proximal insertable tip and an axially opposite distal end, e.g. comprising a connector. The tip may form openings into an internal conduit for draining body fluids, e.g. urine from the body through the catheter to a place of disposal. The connector could be provided e.g. for attaching a collection bag or for attaching a hose for an extension of the catheter. The catheter could also be of the kind forming axially extending outer grooves for conducting the urine along an outer surface.

The medical device could be surface coated, e.g. with a hydrophilic coating to be activated by a swelling medium, e.g. a saline solution.

The compartment could be a pouch, a bottle, a pocket forming part of the package, or any similar means for containing the fluid medium separate from the catheter. In particular, the compartment may comprise an outlet, e.g. formed by a weak point at which the compartment easily ruptures, or formed by other means whereby the fluid medium can be emptied onto the catheter. The weak point could be constituted e.g. by a welding joint which is weak or which contains a weak passage or the weak point could be constituted by a reduced wall thickness of the compartment or by a notch provided in an edge of the compartment to provoke rupturing upon application of a pressure thereto. In addition to, or as an alternative to the weak point, a cutting edge could be provided in an inner surface of the package to facilitate rupturing of the compartment upon contact with the cutting edge.

The fluid medium could be a liquid medium, a gas or powder. As an example, a liquid medium could be the aforementioned saline solution or a similar medium for activating a low surface friction of a hydrophilic medical device, or the liquid could be a lubricant such as a hydrogel. The fluid medium may also comprise an active substance for treating a living being or the medium could comprise an antimicrobial agent. As an example, the medium could be an aqueous solution of an antimicrobial agent such as chlorhexidine digluconate, chlorhexidine dihydrochloride, benzalkonium chloride, hydrogen peroxide, silver chloride, silver sulfadiazine, silver hydantoinate, silver-5,5-dimethylhydantoinate or combinations thereof.

The assembly could be made so that the compartment and the package are opened essentially simultaneously, e.g. so that a seal of the package is broken at the time when the compartment is opened. The compartment could, however, also be opened prior to the opening of the package thereby allowing the fluid medium to wet the surface, or even to react with the surface before the package is opened, or the compartment could be opened after the package has been opened.

The assembly may have a shape which facilitates gripping, in particular for the user having a reduced dexterity. The opening means and possibly also other parts of the assembly may therefore be ergonomically shaped and made in a material, e.g. a synthetic material such as a soft rubber material, or with a surface texture, e.g. knobs, protrusions, ribs or depressions which improve handling, e.g. by the provision of a large surface friction or by the provision of a soft and deformable outer surface in which a handgrip can fixate the assembly or at least the opening means thereof.

To wet the medical device with the liquid medium, the outlet may preferably be located adjacent the medical device, and preferably, the outlet may comprise a conduit which extends in a direction towards the medical device to establish a fluid flow from the compartment towards the device. If the medical device is a catheter to be inserted into the body of a living being, the outlet may advantageously be located close to, or possibly in direct contact with an insertable part of the catheter so that the liquid is applied directly to the part of the catheter where it is needed. In this way, contact between the liquid and parts of the catheter which are touched by the user, could be prevented.

In order further to prevent contact between the liquid and specific areas of the medical device, the assembly may further comprise isolating means, e.g. in the form of a gasket which is located in the container and which seals between inner walls of the container and outer walls of the catheter such that passage of the fluid between the surface of the catheter and the surface of the container is prevented. The gasket could be a ring shaped member located around the medical device. The gasket could be made from any suitable material, e.g. from a resilient material such as rubber or silicone. The gasket could even form part of the medical device or it could form part of the container, e.g. in the form of a protrusion of a surface of the device or container. In order to prevent the liquid from entering into an inner conduit of the catheter, the opening inlets provided in the insertable proximal end of the catheter could be further sealed.

The compartment could be located at a point which during normal handling of the assembly is above the medical device. In that way, the gravity may be used for causing a flow of the liquid across the entire insertable surface of the device. Again, if the device is a catheter, the compartment could be located in the height of, or above the connector. During use, the connector part of the catheter is typically grabbed by the user for manipulating the catheter into, or out of the body, and a dry connector part facilitates this operation. To prevent the liquid from getting in contact with the connector, the container may comprise an elongate sleeve which narrowly encloses the insertable part of the catheter, and the outlet may be located in the sleeve for releasing the liquid directly onto the catheter at a position at a distance from the connector. In one embodiment, the sleeve may have a volume which is in the range of 1 to 20 times, e.g. in the range of 1 to 10 times, such as 1 to 5 times the volume of the insertable part of the catheter. The compartment should preferably contain a sufficient amount of the liquid medium to wet at least an insertable part of the catheter.

As aforementioned, a gasket could prevent the liquid from flowing from the insertable part of the catheter towards the connector part. In this embodiment, a main portion of the compartment may be located on one side of the gasket and the outlet on the other side of the gasket so that the liquid can be stored at a position close to the connector while it is released close to the insertable part of the catheter.

The package may comprise a container part and a detachable closure which interacts with the compartment to open the compartment upon movement of the closure relative to the container. The closure and the container could be joined in a threaded screw joint, by a releasable sealing strip, by an adhesive, by frictional resistance between the parts, or by any kind of engagement between the two parts. Analogously, the container part and the detachable closure could be separated prior to use by breaking, twisting, turning, rupturing squeezing or cutting the parts apart. Typically, the closed container and closure is delivered in a sterile condition.

In one embodiment, the closure for the container forms part of the compartment, whereby the compartment opens upon removal of the closure from the container, and in an alternative embodiment, the closure is located relative to the compartment to enable the closure to press against the compartment and thereby to rupture the compartment. To facilitate the rupturing of the compartment, a cutting edge could be located in the container or in the closure, or the edge could form part of the container or closure.

The closure may be designed so that release of the closure from the container requires opening of the compartment. The opening means may thus be adapted to open the compartment at the latest at the time when the package is opened. In one embodiment, the release of the closure may require the movement of the closure in a direction towards the compartment, and in another embodiment, the closure and compartment may be joined in such a way that the closure can not be removed without rupturing the compartment. In that way, the user may only be able to open the package in the intended way and the user is therefore only able to remove the medical device during a procedure in which the compartment is opened and the liquid medium is released onto the device.

If the medical device has an elongate shape, which is the case for most catheters, the compartment may encircle the catheter whereby a more homogenous wetting can be achieved and whereby space may be saved. As an example, the compartment may have an elongate shape which is twisted around the medical device, or the compartment may comprise an opening through which the medical device can extend. The compartment could e.g. be ring-shaped.

The assembly may form storage space for one or more medical devices, and in one embodiment, the assembly comprises a plurality of individually and mutually isolated packages for accommodation of a plurality of mutually isolated medical devices. In this embodiment, one single compartment may be located with release means for releasing the liquid medium into one of, or all of the packages during a package opening action, or a compartment may be located in connection with each package to wet the medical devices individually upon opening of the packages individually.

In a second aspect, the invention provides a method of wetting a medical device with a liquid medium contained in a compartment, said method comprising the steps of placing the medical device and the compartment in a package so that the liquid medium and the medical device are not in direct contact, and opening the compartment and the package by the same opening action.

In a third aspect, the invention provides a compartment for an assembly according to the first aspect of the invention. The compartment may comprise an opening allowing an elongate medical device to extend through the compartment.

Any of the features described in connection with the first aspect may apply also to the second and third aspects.

DETAILED DESCRIPTION OF THE PREFERRED EMBODIMENTS

Further scope of applicability of the present invention will become apparent from the following detailed description and specific examples. However, it should be understood that the detailed description and specific examples, while indicating preferred embodiments of the invention, are given by way of illustration only, since various changes and modifications within the spirit and scope of the invention will become apparent to those skilled in the art from this detailed description.

Figures 1A, 1B, 1C, 1D:
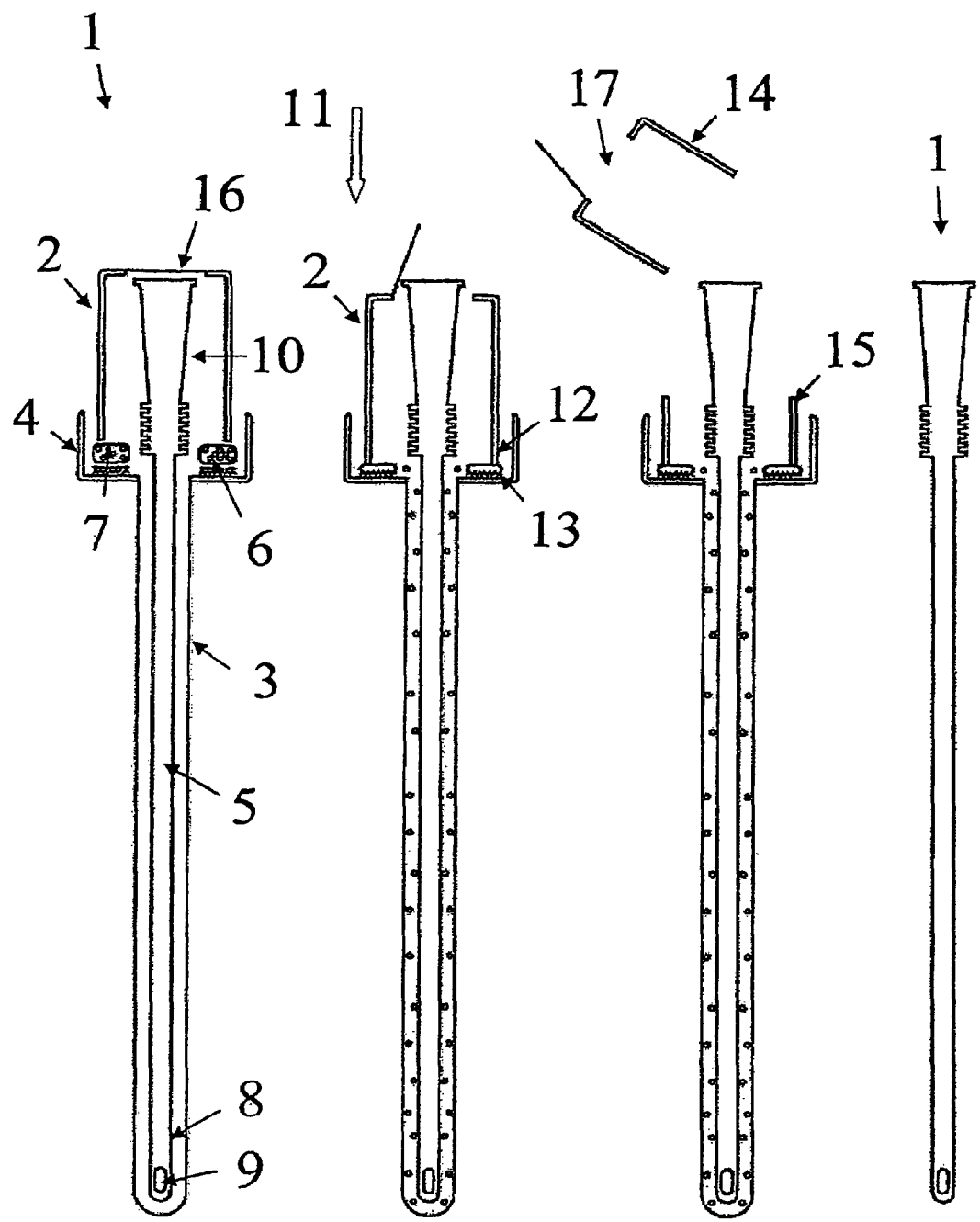
FIGS. 1a, 1b, 1c and 1d illustrate an opening sequence of an assembly according to the present invention.

FIGS. 1a, 1b, 1c and d illustrate an assembly for wetting a medical device with a liquid medium. The assembly comprises a package having a closure 2 and a container having an elongate sleeve 3 which narrowly encloses the insertable part of the catheter and which is connected to a cup shaped top part 4 which is open upwardly. The package accommodates a urinary catheter 5 and further accommodates a compartment 6 with the liquid medium, indicated by bubbles 7. The liquid medium is kept separate from the catheter until the compartment is opened and emptied prior to use of the catheter. The catheter comprises a proximal end 8 shaped for insertion into the body of the user and comprising inlet openings 9 for body substances to be drained into an inner conduit of the catheter. The opposite distal end of the catheter is provided with a connector part 10 from which the body fluids can be drained to a place of disposal. To reduce the amount of the liquid medium which is necessary for wetting the insertable part of the catheter, the container forms an elongate sleeve which narrowly encloses the proximal end of the catheter.

FIGS. 1a, 1b, 1c and 1d illustrate the assembly 1 in four sequences of an opening procedure. In FIG. 1a, the catheter is sealed, e.g. hermetically, in the sterilised package. In FIG. 1b, the user has broken the seal between the closure 2 and the container, comprising the sleeve 3 and the top part 4, by pushing the closure in the direction indicated by the arrow 11 whereby the edge 12 of the closure pushes the compartment towards the sharp pointed cutting edge 13. This breaks the sealing and the compartment is emptied whereby the liquid (indicated by the bubbles) flows downward into the elongate sleeve 3. In FIG. 1c, the closure is removed from the container to enable removal of the catheter from the package. To remove the closure, the user may either pull the closure in an upward direction, opposite the direction indicated by the arrow 11, or the user may break a top portion 14 of the closure free from a bottom portion 15. The disclosed assembly contains an additional opening feature consisting of a seal 16, e.g. a thin foil which is bonded to cover an opening 17 in a top face of the closure. During the initial pushing of the closure in the direction of the arrow 11, the distal part of the catheter penetrates the foil or releases the foil from its contact with the closure to enable the catheter to be removed from the package without further opening of the package. The top portion 14 of the closure could be made from a soft, flexible material which could be squeezed into contact with the catheter merely by finger pressure, and the top portion may constitute an applicator facilitating non contaminating manipulation of the catheter without direct contact between the hands of the user and the catheter, c.f. also FIG. 8.

Due to the relationship between the distance between the catheter and the foil and the distance between the closure and the compartment, the compartment is opened prior to or, at the latest, simultaneously with the opening of the package. In that way, removing the catheter from the package in the intended way before the compartment has been opened is prevented, and wetting of the catheter prior to use is ensured. In FIG. 1d, the catheter is removed from the package.

Figures 2A, 2B, 2C, 2D:
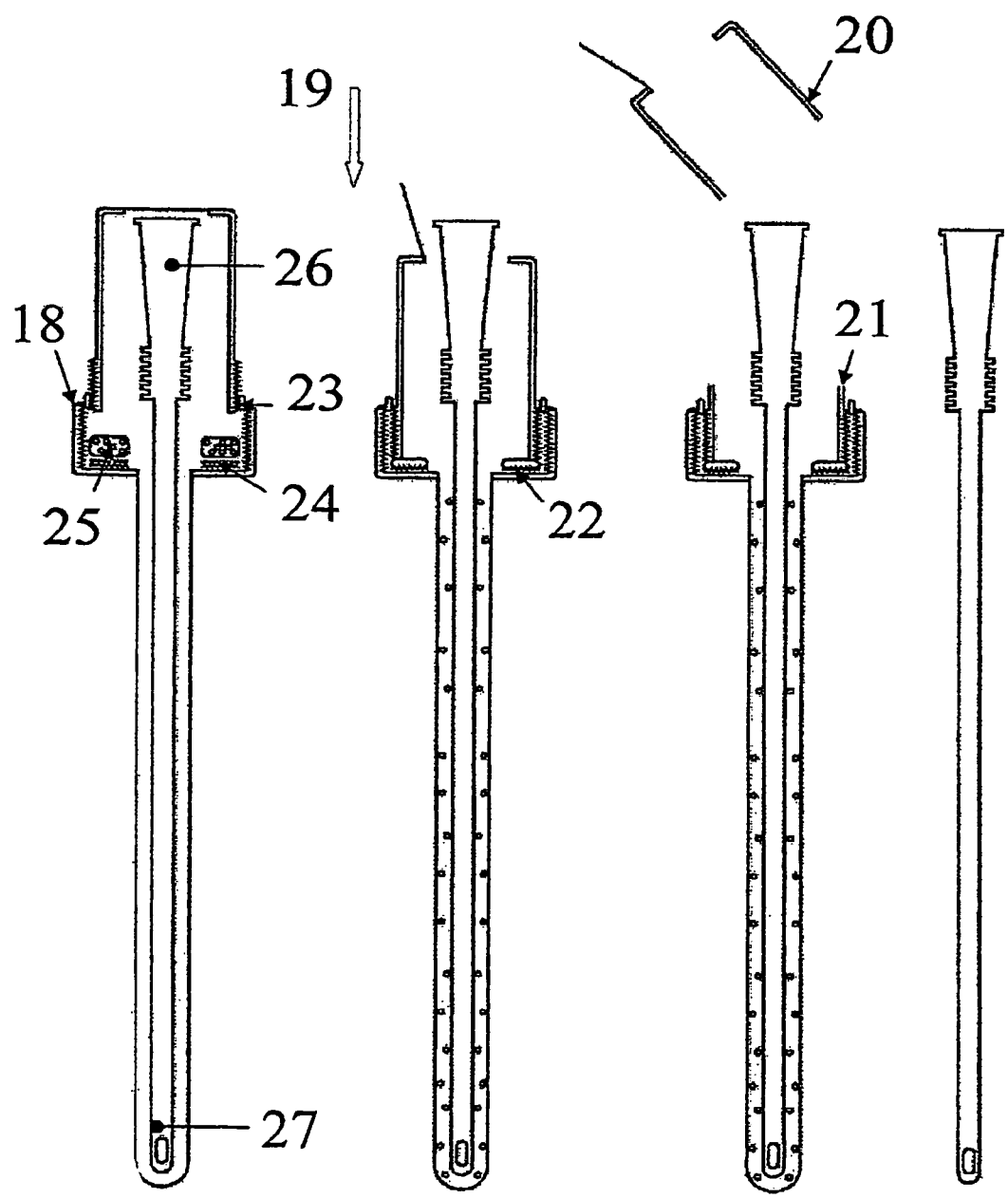
FIGS. 2a, 2b, 2c and 2d illustrate an opening sequence of an alternative embodiment of the invention.

FIGS. 2a, 2b, 2c and 2d illustrate an alternative embodiment of the assembly in which the closure is joined to the container via a threaded joint 18. To open the package as shown in FIG. 2a, the user screws the closure as far as possible in the direction indicated by the arrow 19 until the top portion 20 of the closure breaks off from the bottom portion 21 (see FIGS. 2b and 2c). At this point, the compartment has been pushed downwardly onto the sharp pointed edge 22 whereby it opens. The limitation of the travel of the closure in the downward direction could be defined e.g. by the length of the threaded inner surface of the container and/or by the threaded outer surface of the closure, or the travel may be defined by the edge 23 of the closure reaching the bottom 24 of the surface on which the compartment 25 is supported. Compared with the embodiment disclosed in FIGS. 1a, 1b, 1c and 1d, the compartment is located adjacent the catheter at a position more distant from the connector part 26 of the catheter, and the liquid substance is thus released closer to the proximal, insertable tip 27 on a part of the catheter which is to be inserted into the body of a patient and where a reduced friction and/or an improved antimicrobial protection is therefore particularly desired. In FIG. 2d, the catheter is removed from the package.

Figures 3A, 3B, 3C:
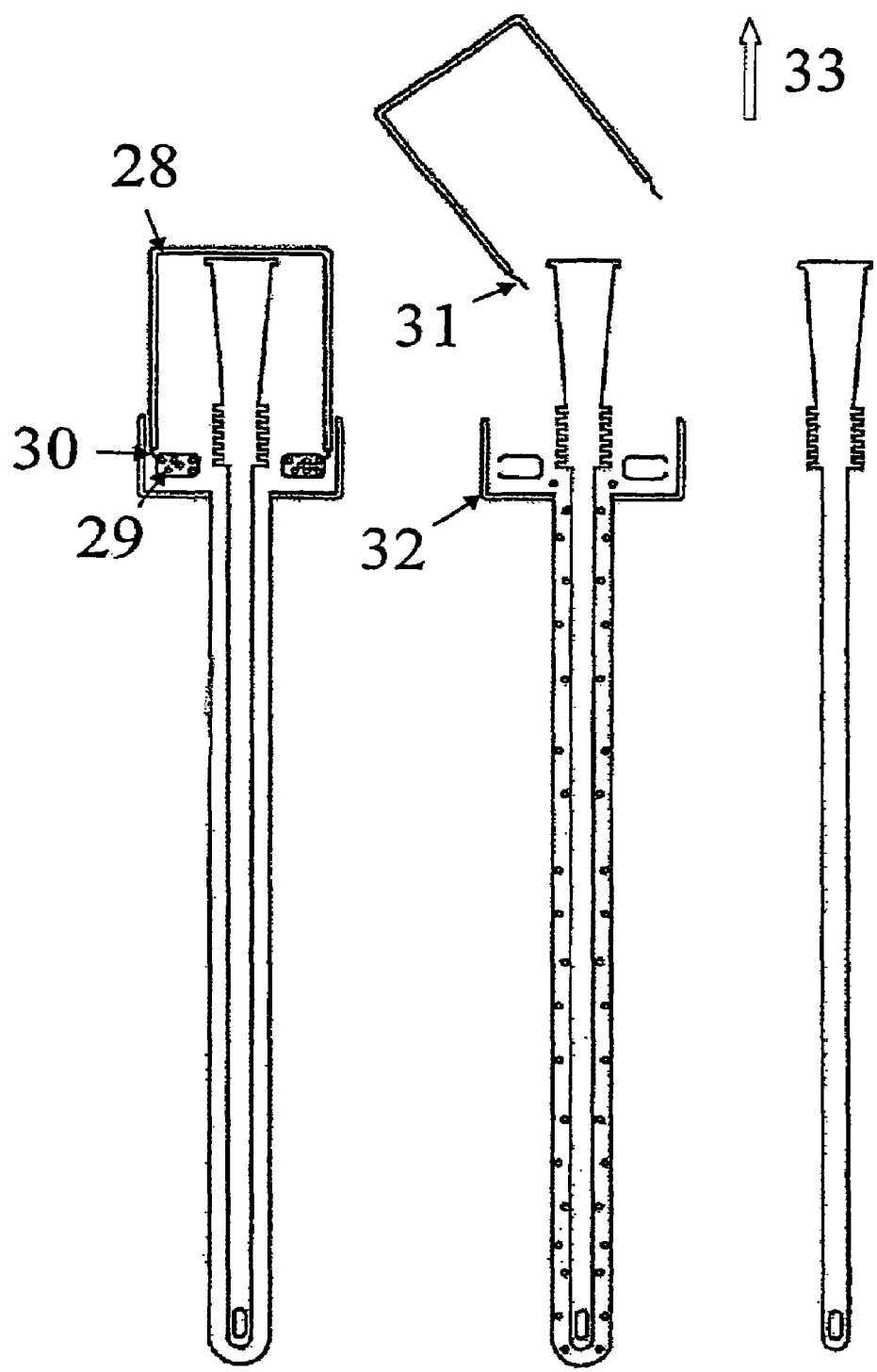
FIGS. 3a, 3b and 3c illustrate an opening sequence of an alternative embodiment of the invention.

FIGS. 3a, 3b and 3c illustrate an embodiment of the assembly in which the closure 28 forms part of, or is attached to the compartment 29 via the connecting portion 30 comprising a resilient strip 31 fastened to the closure and to the compartment, as shown in FIG. 3a. When the closure is removed from the container 32 in an upward direction, indicated by the arrow 33 and shown in FIG. 3b, the connecting portion follows the closure and thereby ruptures the compartment from which the content is discharged onto the insertable part of the surface of the catheter. In FIG. 3c the catheter is removed from the package.

Figure 4:
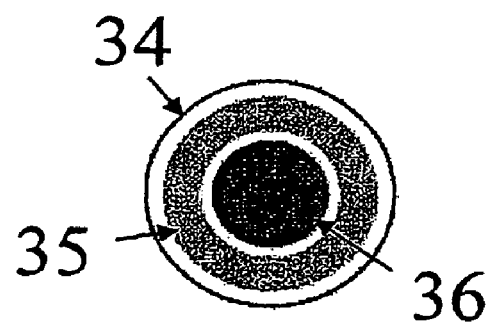
FIG. 4 illustrates a top view of an assembly according to the invention.

FIG. 4 illustrates a top view of the assembly in an embodiment with a tubular/circular shape. The outer periphery of the closure 34 encircles a compartment 35 which encircles the catheter 36.

Figure 5A:
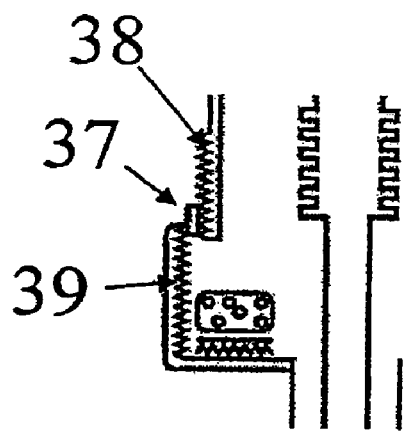
FIGS. 5a and 5b illustrate different sealing joints between the container and top part of the assembly.
Figure 5B:
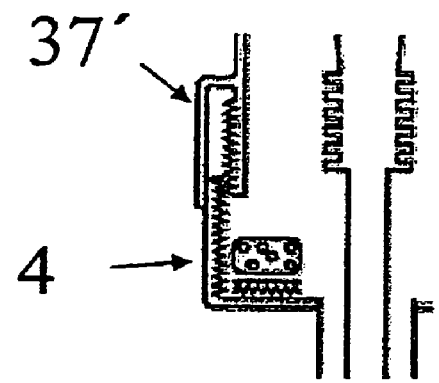

FIG. 5a illustrates an assembly wherein a sealing is symbolized by sealing means 37 located between the threads 38 of the closure and the threads 39 of the container to seal the package. In FIG. 5b sealing means 37' is illustrated which is located to enclose the cup shaped top part 4.

Figure 6:
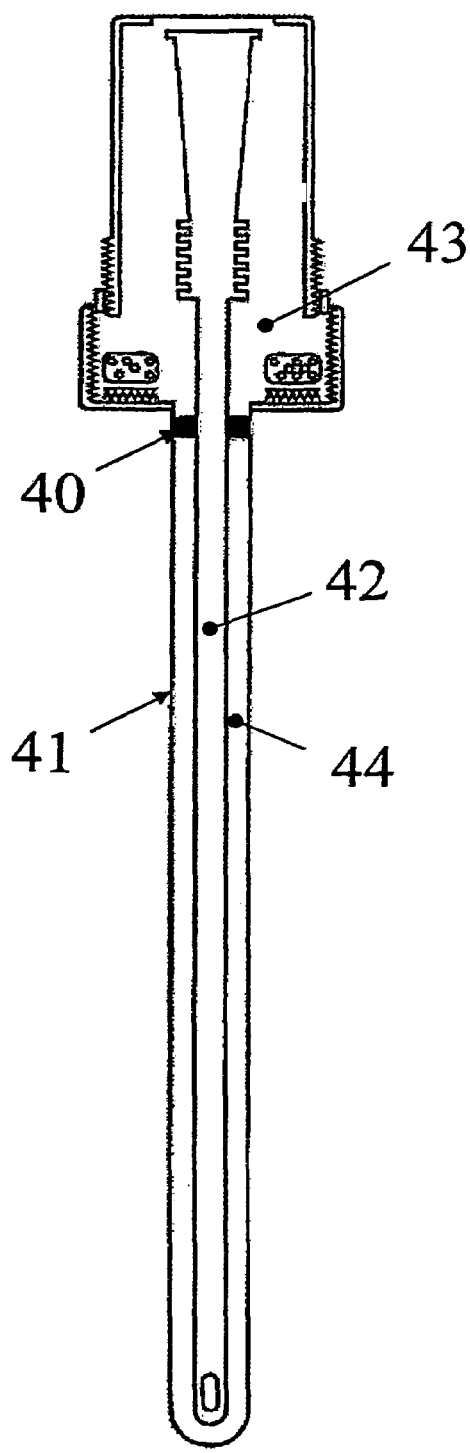
FIG. 6 illustrates an assembly with a gasket.

FIG. 6 illustrates an assembly wherein a gasket 40 is located between an inner surface of a sleeve-formed part 41 of the container and an outer surface of the catheter 42. The gasket separates the package into a first storage space 43 and a second storage space 44 between which the liquid is prevented from passing. The insertable part of the catheter is located in the second storage space and the connector is located in the first storage space.

Figure 7:
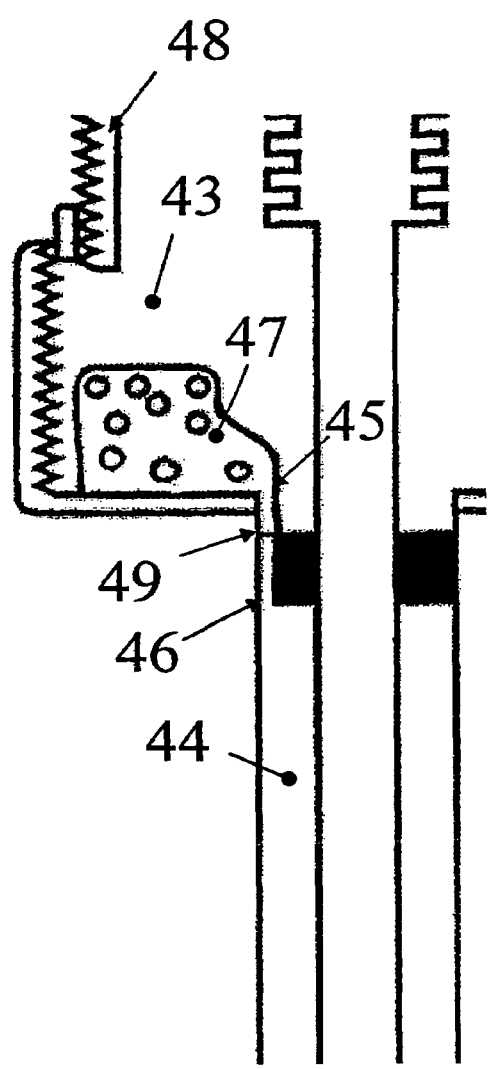
FIG. 7 illustrates an enlarged view of a top part of the assembly illustrated in FIG. 6.

FIG. 7 illustrates an enlarged view of one embodiment of an assembly with a gasket. The compartment comprises an elongate passage 45 which extends between the first and second spaces so that the compartment can be contained in the first space while the outlet 46 releases the liquid into the second space. The compartment 47 is made from a flexible material, and when the closure 48 is pushed downwardly towards the compartment, the internal pressure of the liquid increases to a point at which the seal 49 is severed and the liquid is emptied into the second space.

Figure 8:
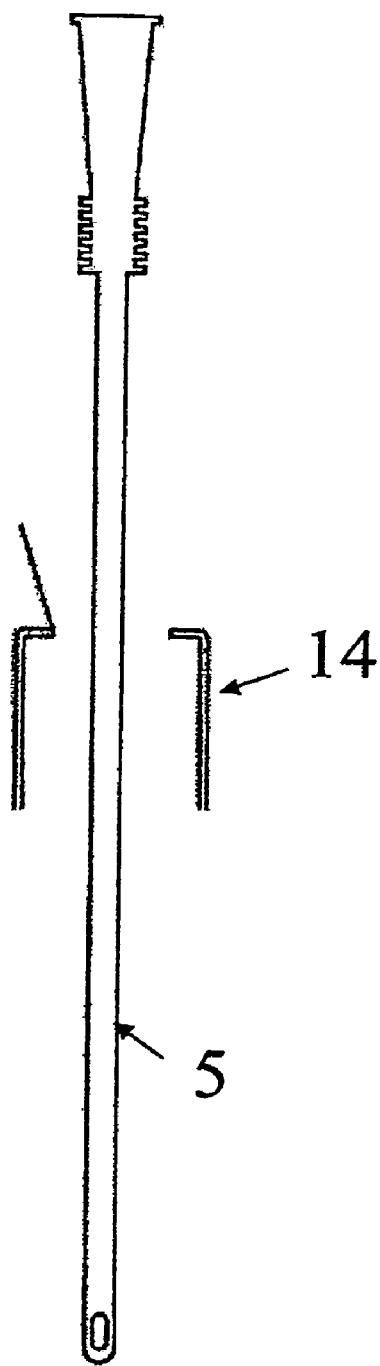
FIG. 8 illustrates the use of the top part as an applicator for non contaminating manipulation of the catheter.

FIG. 8 illustrates the use of the removable closure part or top portion 14 for non-contaminating insertion of the catheter. The top portion is made from a soft resilient material which after release from the container can be squeezed into engagement with the catheter 5 and be used to isolate the outer surface of the catheter from the hands of the user.

Figure 9A:
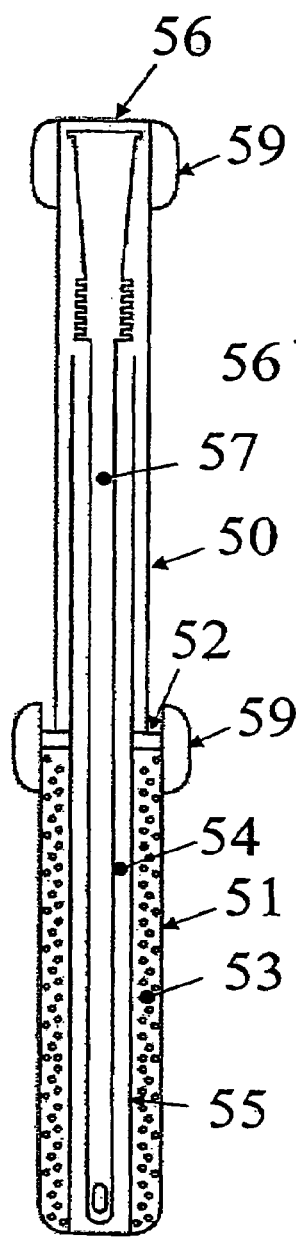
FIGS. 9a, 9b, 9c and 9d illustrate an alternative embodiment of the assembly.
Figure 9B:
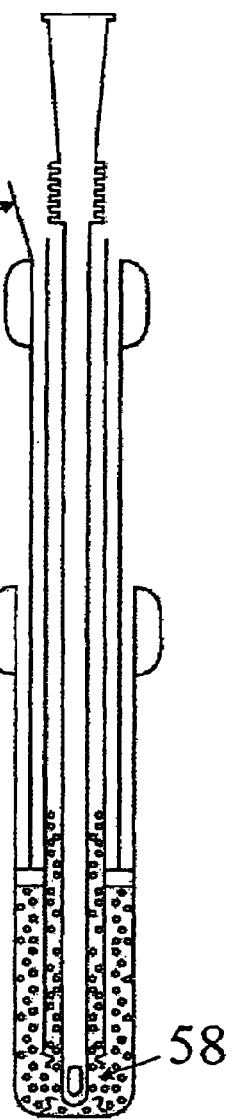
Figure 9C:
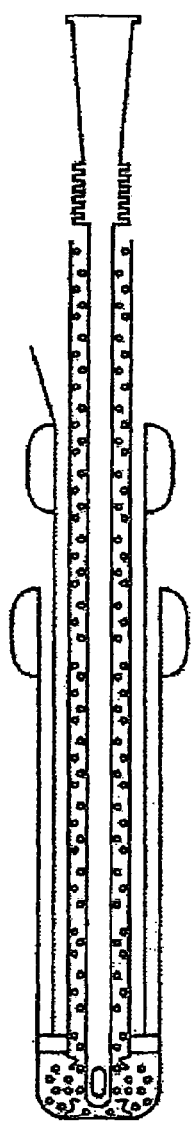
Figure 9D:

FIGS. 9*a*, 9*b*, 9*c* and 9*d* illustrate an alternative embodiment of the invention wherein the container comprises a first section 50 and a second section 51 joined in a telescopic joint via the piston packing 52. The second section comprises a compartment 53 for the fluid medium and a cavity 54 for accommodation of the medical device. The fluid medium is separated from the medical device by the wall 55 as shown in FIG. 9*a*. The piston packing is attached to, or forms part of the first section and engages an inner surface of the second section. During the opening procedure, the first section is pushed into the second section, or more specifically, the first section is pushed into the compartment. During this movement of the first section relative to the second section as shown in FIGS. 9*b* and 9*c,* the top foil 56 is released whereby the catheter 57 or similar medical device is pushed out of the package, and the pressure of the fluid in the compartment is increased until a point where a section 58 of the wall 55 ruptures and the fluid medium indicated by the bubbles is pushed from the compartment into the cavity housing the medical device whereby the fluid and the device is brought in contact. To enable the rupturing of the wall 55, the wall may comprise a weak point, e.g. a notch or an incision or similar feature whereby the strength of the wall is reduced locally. As an alternative to the rupturing of the wall, the wall may comprise an opening which is sealed by a closure, e.g. a strip of a resilient tape etc. which is removed from the opening under influence of the increasing pressure of the fluid medium when the first section is moved relative to the second section. The protrusions 59 are provided to facilitate gripping the package by the hands. In FIG. 9*d* the catheter is removed from the package.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An assembly for wetting a medical device with a fluid medium, said assembly comprising a package accommodating the medical device, a compartment accommodating the fluid medium so that the fluid medium is not in contact with the medical device, and an opening mechanism adapted for a combined opening action by which the package as well as the compartment are opened.

2. The assembly according to claim 1, wherein the opening mechanism is adapted to open the package and the compartment by movement of a first component relative to a second component of the assembly.

3. The assembly according to claim 2, wherein the first component is adapted to be moved into the compartment which forms part of the second component, whereby the fluid medium is released onto the medical device.

4. The assembly according to claim 1, wherein the opening mechanism is adapted to prevent exposure of the medical device without a preceding opening of the compartment.

5. The assembly according to claim 4, wherein the opening mechanism is adapted for opening of the compartment at the latest simultaneously with opening of the package.

6. The assembly according to claim 1, wherein the package includes a container with an opening for exposing the medical device from the package, the opening being closed by a detachable closure, wherein the closure interacts with the compartment to open the compartment upon movement of the closure relative to the container.

7. The assembly according to claim 6, wherein the closure interacts with the compartment to open the compartment upon removal of the closure from the package.

8. The assembly according to claim 1, further comprising a cutting edge which is formed to perforate the compartment upon operation of the opening mechanism.

9. The assembly according to claim 8, wherein the cutting edge forms part of the closure.

10. The assembly according to claim 8, wherein the package includes a container and the cutting edge forms part of the container.

11. The assembly according to claim 1, wherein the compartment encircles the medical device.

12. The assembly according to claim 1, wherein the fluid medium contains an antimicrobial substance.

13. The assembly according to claim 1, wherein the package accommodates the compartment.

14. The assembly according to claim 1 wherein the package includes a container and the medical device is a catheter, said container forming an elongate sleeve for accommodation of at least an insertable lenght of the catheter.

15. The assembly according to claim 1, wherein the medical device includes an insertable part adapted to be inserted into the body of a living being and the compartment includes an outlet located to release the fluid medium onto the insertable part.

16. The assembly according to claim 1, wherein said compartment includes an opening allowing an elongate medical device to extend through the compartment.

17. A method of wetting a medical device with a fluid medium contained in a compartment, said method comprising the steps of placing the medical device and the compartment in a package so that the fluid medium and the medical device are not in direct contact during storage, and opening the compartment and the package by the same opening action by which the fluid and the medical device are brought into contact.

* * * * *

UNITED STATES PATENT AND TRADEMARK OFFICE
CERTIFICATE OF CORRECTION

PATENT NO. : 7,571,804 B2
APPLICATION NO. : 11/070283
DATED : August 11, 2009
INVENTOR(S) : Bruun et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 864 days.

Delete the phrase "by 864 days" and insert -- by 1268 days --

Signed and Sealed this

Twentieth Day of April, 2010

David J. Kappos
*Director of the United States Patent and Trademark Office*